United States Patent [19]

Wong

[11] Patent Number: 4,591,721

[45] Date of Patent: May 27, 1986

[54] OXYGEN ANALYSIS EMPLOYING ABSORPTION SPECTROSCOPY

[75] Inventor: Jacob Y. Wong, Santa Barbara, Calif.

[73] Assignee: Andors Analyzers Incorporated, Berkeley, Calif.

[21] Appl. No.: 659,253

[22] Filed: Oct. 10, 1984

[51] Int. Cl.⁴ ............................................. G01J 1/42
[52] U.S. Cl. .................................................... 250/373
[58] Field of Search ......................................... 250/373

[56] References Cited

U.S. PATENT DOCUMENTS

| | | | |
|---|---|---|---|
| 3,449,565 | 6/1969 | Barringer | 250/373 |
| 4,096,388 | 6/1978 | Wong | 250/373 |
| 4,192,996 | 3/1980 | Kronick et al. | 250/373 |

OTHER PUBLICATIONS

"Pen-Ray Lamps . . . Ultraviolet Sources for Research and Industry," 1977, by Ultra-Violet Products, Inc., pp. 1-11.

Primary Examiner—Janice A. Howell
Attorney, Agent, or Firm—Fitch, Even, Tabin & Flannery

[57] ABSTRACT

A method and apparatus are described for detecting the presence and amount of elemental oxygen in a sample cell. The intensity of extreme ultraviolet light passing through the sample cell at a wavelength band overlapping at least one of the Schumann-Runge absorption lines of oxygen is detected and compared with a predetermined non-absorbed condition of the ultraviolet light. The non-absorbed condition may be achieved by narrowing the wavelength band such that the band does not overlap the Schumann-Runge absorption line, or may be achieved by detecting the ultraviolet light passing through a reference cell. Also described is a novel ultraviolet source in which a cold zone captures neutral atoms of the emission gas to reduce the affect of resonance absorption of emitted ultraviolet light by such neutral atoms.

9 Claims, 5 Drawing Figures

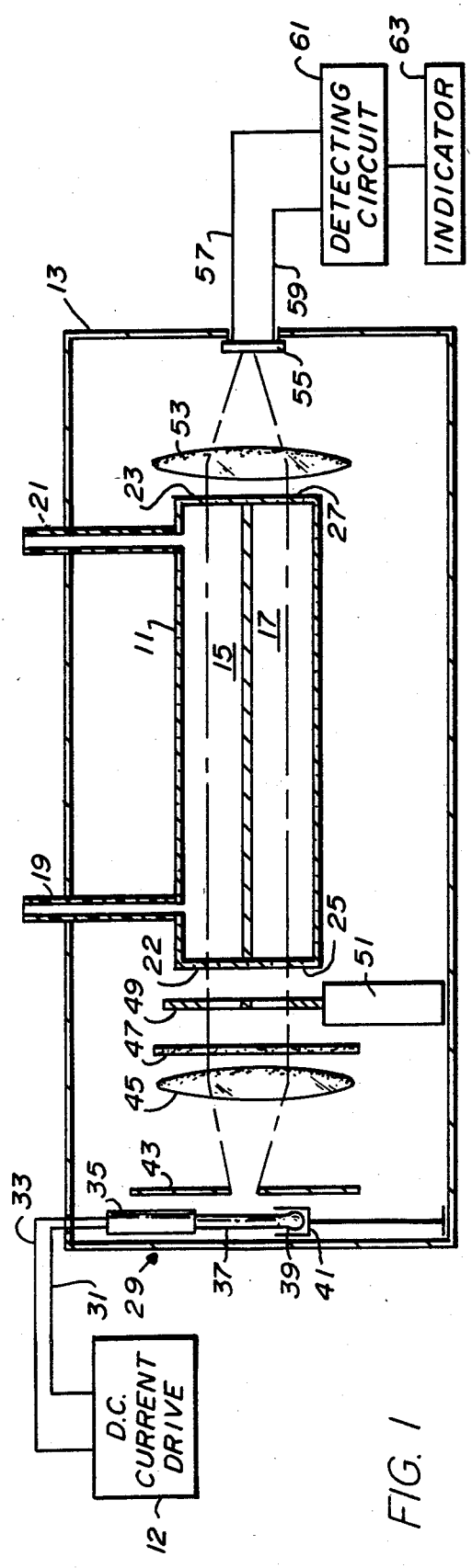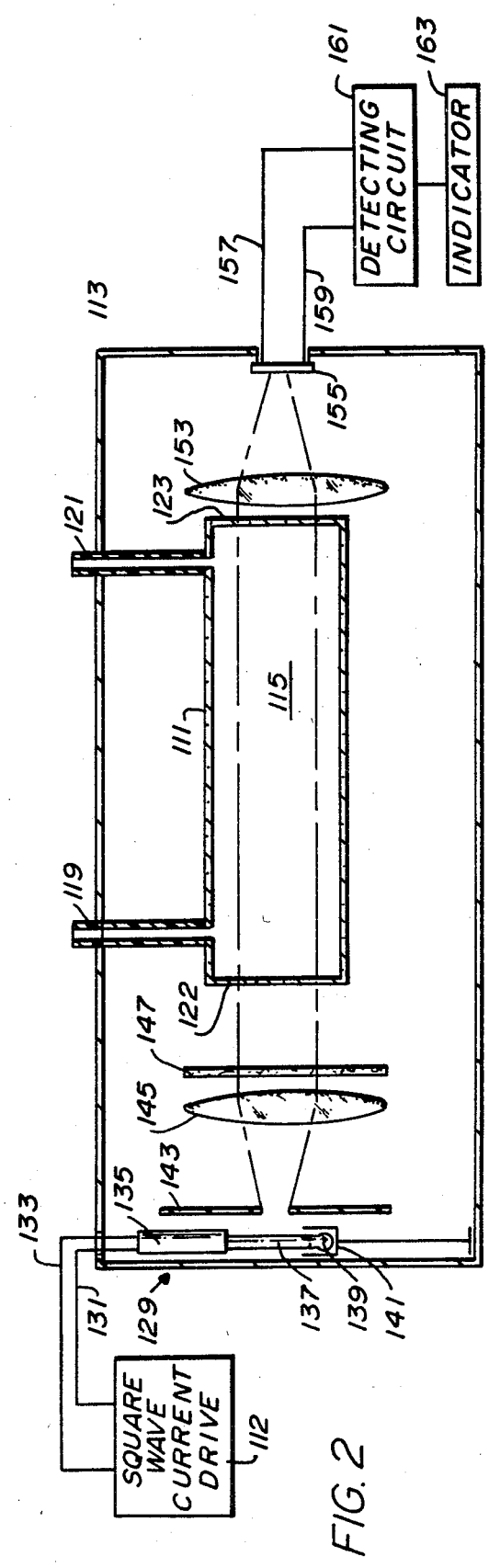

OXYGEN ANALYSIS EMPLOYING ABSORPTION SPECTROSCOPY

This invention relates generally to the detection and measurement of elemental oxygen in a mixture of gases and, more particularly, to oxygen detection by means of improved method and apparatus employing the principles of electromagnetic radiation absorption (absorption spectroscopy).

The use of the principles of absorption spectroscopy for detecting and measuring gas concentration has met with significant commercial success in a number of applications. For example, infrared absorption spectrometers are commonly utilized in the measurement of carbon dioxide and various hydrocarbons. The relative lack of complexity, low weight and compactness, and speedy response of the spectroscopic approach to gas measurement offers significant advantages over other possible approaches for many applications.

The detection and measurement of elemental oxygen by gas absorption spectroscopy has thus far defied a solution which is commercially practical. Two prior attempts in this area are disclosed in Wong, U.S. Pat. No. 4,096,388 (1978) and Kronick et al, U.S. Pat. No. 4,192,996 (1980). Both of these patents disclose techniques for measuring gaseous oxygen with ultraviolet absorption at certain specific sharp lines of the so-called Schumann-Runge absorption band of molecular oxygen (in the extreme ultraviolet wavelength spectrum).

The Schumann-Runge band is potentially very useful for measuring oxygen for several reasons. Very few other gases absorb in the Schumann-Runge band, thereby minimizing interference problems. The particular absorption lines of oxygen in this range are also very strong - stronger than oxygen absorption lines at longer wavelengths. Finally, the Schumann-Runge absorption lines of oxygen are very narrow, further minimizing potential interference problems caused by absorption by other gases.

In order to provide a source of ultraviolet radiation in a system wherein the Schumann-Runge absorption lines are to be utilized, there are two possible approaches. One approach is to employ a very broad-band ultraviolet source and to provide adequate filtering, either at the source or at the detector, to suitably narrow the bandwidth to the desired Schumman-Runge absorption line. Unfortunately, filters of adequately narrow band-width are not readily available. Moreover, there is a significant increase in cost due to the expensive nature of such narrow band filters and due to the high power requirements of broad band ultraviolet sources.

For these reasons, both Wong and Kronick, et al utilize a mercury arc discharge lamp as their ultraviolet source. Low pressure mercury discharge lamps utilizing the first emission state of mercury to emit photons are sometimes referred to as Hgl ultraviolet sources. A lamp of this type is commercially available as the model 11SC-1 available from Ultraviolet Products Inc., San Gabriel, Calif. Such a lamp emits ultraviolet light at a number of wavelengths including a band at 1,849.57 angstrom units. This atomic emission band is spectrally very narrow and under normal operating conditions does not significantly overlap the 1,849.38 angstrom absorption line of the Schumann-Runge system (N=9,0-8 band).

Kronick, et al employs a lamp of this general type containing isotopes of mercury which cause a shifting in the emission band. By using two different combinations of isotopes, two closely spaced ultraviolet radiation emission lines are created in the vicinity of the 1,849.57 angstrom Hgl atomic transition line. However, even the isotopically shifted lines are too narrow under normal operating conditions to significantly overlap the desired Schumann-Runge band to provide adequate modulation for the measurement. Furthermore, the use of different mercury isotopes in the proposed scheme of Kronick, et al is laborious and expensive, rendering the approach quite unsuitable for commercial purposes.

In the Wong patent, an Etalon (trademark) filter is used to select two wavelengths from the ultraviolet source, one of which is strongly absorbed only by oxygen and the other of which is weakly absorbed by oxygen and other common gases, such as nitrogen, water vapor, and carbon dioxide. By comparing the difference in absorption at the two wavelengths, an indication of the amount of oxygen in the sample may be obtained. In the scheme disclosed in the Wong patent, however, an elaborate Fabry-Perot Etalon (trademark) filter is required which is costly and difficult to build. Moreover, it is suggested that spectral broadening of the 1,849.57 angstrom unit emission line of the Hgl discharge lamp may be obtained by Lorentz or collision broadening. This is not achievable as suggested in Wong's patent. Thus, although the described system would work in connection with a broad band source, such as a deuterium lamp, use with the lower cost mercury discharge lamp is unworkable. This is because operation of a standard Hgl discharge lamp at currents sufficient to achieve a broadening of at least 3 angstroms full width at half the maximum (FWHM) causes the output from the lamp to fall to such a low level as to make impossible any meaningful oxygen measurement.

It is an object of the present invention to provide an improved method and apparatus for detecting and measuring elemental oxygen in a gas sample.

Another object of the invention is to provide an improved ultraviolet absorption spectrometer technique for measuring elemental oxygen in a mixture of gases.

Another object of the invention is to provide an improved ultraviolet source for use in an oxygen measurement system of the type described.

Other objects of the invention will become apparent to those skilled in the art from the following description, taken in connection with the accompanying drawings wherein:

FIG. 1 is a schematic drawing illustrating apparatus constructed in accordance with the invention;

FIG. 2 is a schematic drawing illustrating a further embodiment of the apparatus of the invention;

Figure 3:
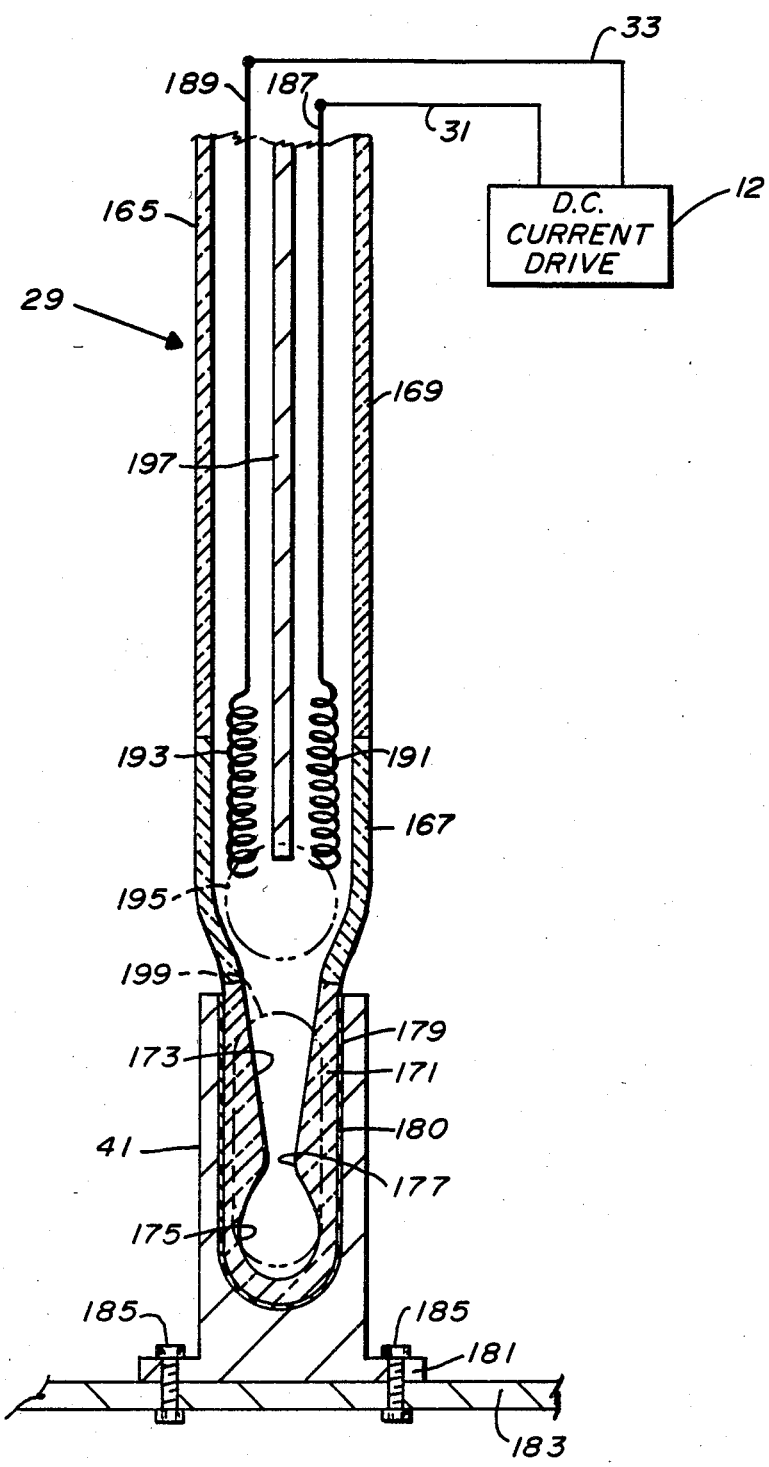
FIG. 3 is a schematic cross-sectional view of an ultraviolet source for use in the apparatus of either FIGS. 1 or 2.

Very generally, in the method and apparatus of the invention, the presence and amount of elemental oxygen is detected in a sample cell. Extreme ultraviolet light is passed through the sample cell at a wavelength band FWHM of less than about 0.50 angstroms. The band overlaps at least one of the Schumann-Runge absorption lines of oxygen at a substantial intensity. The intensity of the ultraviolet light passing through the sample cell is detected and compared with a predetermined non-absorbed condition of the ultraviolet light. This may be achieved by narrowing the wavelength band such that the band does not overlap any Schumann-Runge absorption lines of oxygen at a substantial intensity. Alternatively, this may be done by directing the ultraviolet light through a reference cell which provides a predetermined reference intensity of the light.

Spectral broadening of the ultraviolet light to sufficiently overlap the desired Schumann-Runge absorption line is achieved by an improved ultraviolet source including an envelope for confining a discharge gas and a pair of electrodes which develop an arc within the envelope in a hot zone to cause emission of photons from a discharge gas contained within the envelope. A reservoir communicates with the envelope at an orientation adapted to be below the hot zone with the lamp in an operative position. The reservoir is shaped so as to collect condensate of the discharge gas and so as to retain the condensate in a cold zone within the reservoir. The reservoir is externally cooled.

Referring now more particularly to FIG. 1, a gas cell 11 is enclosed in an airtight enclosure 13. The gas cell is divided into two chambers 15 and 17 which provide, respectively, the sample cell for the gas to be analyzed and a reference cell. The reference cell is sealed enclosing a suitable reference gas, such as nitrogen. The sample cell 15 is provided with an inlet passage 19 and an outlet passage 21. Gas to be analyzed enters the sample cell 15 through the inlet passage and exits through the outlet passage in a sequence which may be suitably determined by valves and other ancillary components, not shown. Each end of the sample cell 15 and the reference cell 17 is provided with a ultraviolet transparent window 22, 23, 25, and 27, respectively.

A source of ultraviolet light in the extreme spectrum centered on the wavelength 1849.57 angstroms is provided by an HgI lamp 29 constructed in accordance with the invention. The lamp 29, which is described with more particularity below, is connected to a suitable source of current 12 by a pair of leads 31 and 33. The leads pass through the air-tight enclosure 13 and are connected to the electrodes of the lamp 29, as will be described below, inside of a suitable lamp support housing 35. The lamp, described with greater particularity below, includes a quartz envelope 37, the lower end of which includes a specially shaped reservoir 39 surrounded by a heat sink 41.

Ultraviolet light from the lamp 29 is passed through an aperture plate 43 and through a lens 45 of a material, such as Suprasil (trademark) which transmits all wavelengths in the mercury ultraviolet spectrum. The lens collimates the light and expands the beam so as to pass through both the sample cell 15 and the reference cell 17. Between the lens 45 and the cell enclosure 11 is a low pass filter 47 and a chopper wheel 49. The low pass filter excludes both the 1930 angstrom units line and the 2537 angstrom units lines of HgI emission. Such exclusion is preferred to avoid reduction in modulation at 1849.57 angstrom units because of the much higher power radiated at the excluded wavelengths. The chopper wheel 49 is rotated by a motor 51 to periodically and alternately interrupt the light passing into the sample cell and the reference cell to provide a pulsed beam through alternative cells as is well known in the spectrometer art.

At the far end of the cell enclosure 11, a second lens 53, of like material to that of the lens 45, is positioned to direct the light passing through both the sample cell 15 and the reference cell 17 to a detector 55. The detector may be any suitable light sensitive device but, in the illustrated embodiment, is preferably an ultraviolet enhanced silicon photodiode. The output of the photodiode 55 is carried by a pair of suitable leads, 57 and 59, to a detecting circuit 61 for processing the signals. The detecting circuit 61 may be of any suitable type known to those skilled in the art. For example, detecting circuits capable of processing signals of this general type are shown and described in U.S. Pat. Nos. 4,027,972 and 4,013,260. The output of the detecting circuit is provided to a suitable indicator 63, such as a digital display, for indicating the percentage of oxygen present in the sample cell 15.

Figure 4:
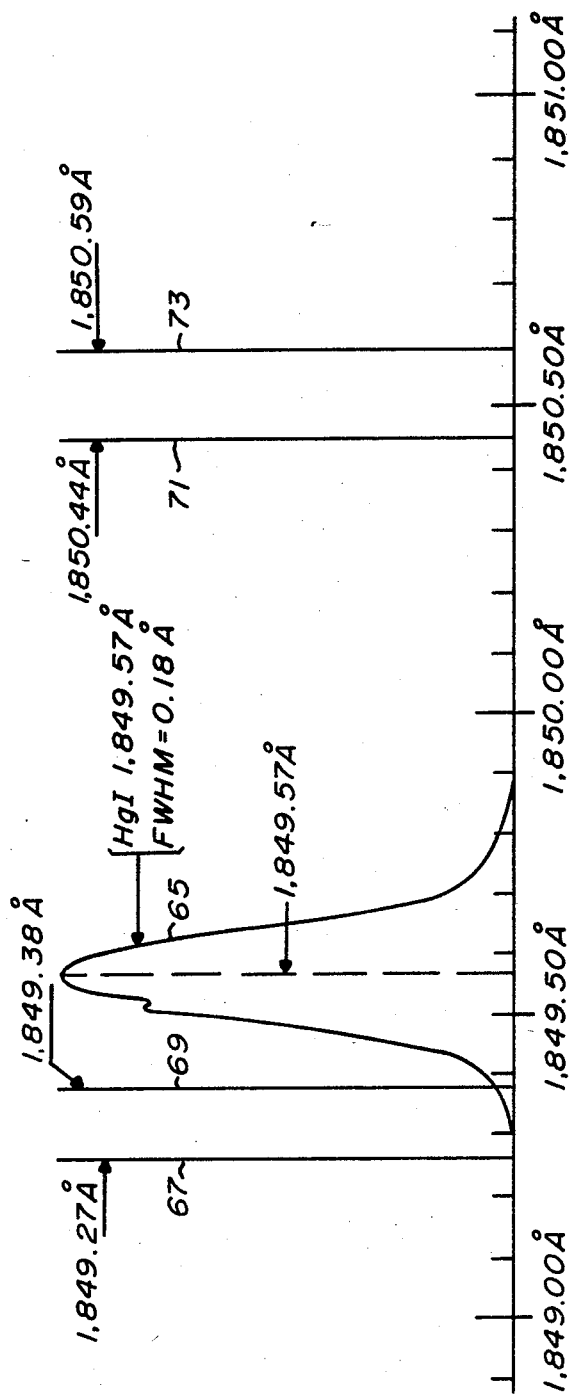
FIG. 4 is a graph illustrating the output of a typical Hgl arc lamp running at normally rated current capacity with nominal line width, compared with respect to the Schumann-Runge absorption lines of oxygen.

Referring for the moment to FIG. 4, and by way of digression, a graph is shown illustrating the output of a typical HgI arc lamp. The output curve of the lamp is shown at 65 and is centered about the 1849.57 angstrom wavelength. The nominal line width is FWHM 0.18 angstroms. Accordingly, very little spectral overlap occurs with any of the Schumann-Runge absorption lines of oxygen, illustrated at 67 (1849.27 angstroms), 69 (1849.38 angstroms), 71 (1850.44 angstroms), and 73 (1850.59 angstroms). Thus, the employment of such a lamp, for example the model UVP11SC-1, running at normally rated current capacity would result in very little absorption of the ultraviolet by any of the Schumann-Runge absorption lines.

As previously mentioned, the Wong U.S. Pat. No. 4,096,388 cited above, suggests that the bandwidth of the emission of an HgI lamp may be broadened by driving the lamp at a current several times higher than its rated capacity. In fact, however, this has proved to be impractical. To substantially cover the 1849.38 angstrom absorption line of oxygen (line 69 in FIG. 4), spectral broadening of the emission of the lamp must provide a FWHM of at least 3 angstroms. However, even at an FWHM of 0.5 angstroms, as the internal lamp pressure increases, quenching of the emission begins through resonance absorption of the nominal emission wavelength by neutral mercury atoms that are vaporized from the mercury reservoir within the lamp on account of the concomitant increase in internal lamp temperature. The net result is that there is a negligible output from the HgI discharge lamp when it is driven to sufficiently increase the bandwidth to make any meaningful oxygen measurement.

Figure 5:
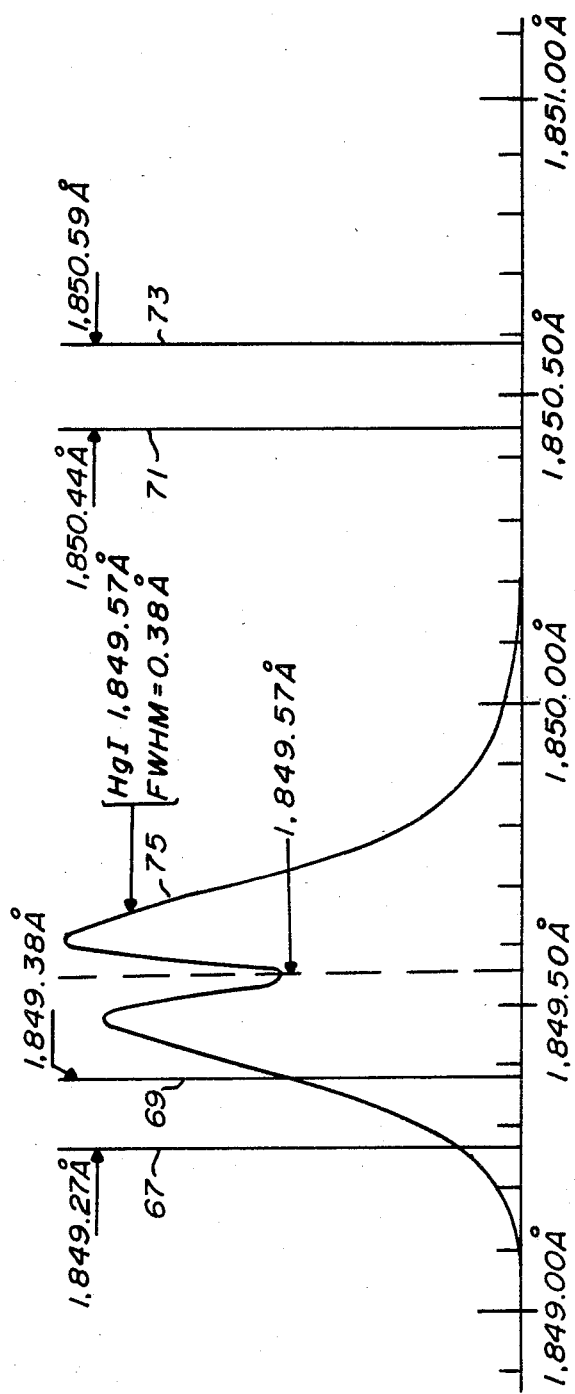
FIG. 5 is a graph illustrating the output of the lamp of FIG. 3 when operated at three times normally rated current capacity, compared with the Schumann-Runge absorption lines of oxygen.

Referring now to FIG. 5, it may seen that the curve 75 representing the 1849.57 angstrom output of the HgI arc lamp is significantly broader than that of the curve 65 in FIG. 4. This broadened bandwidth is FWHM 0.38 angstroms and results from the improved lamp construction described below. Because of the significant spectral line broadening of the HgI output, there is a significant spectral overlap with the 1849.38 angstrom absorption line of oxygen in the Schumann-Runge range. The absorption lines of oxygen are indicated in FIG. 5 and are provided with the same numerals as those in FIG. 4. The dip in the middle of the curve 75 results from the absorption of the lamp output by neutral mercury atoms in the region of the arc. This absorption, however, will be seen to not affect the curve in the region of the absorption line 69.

Returning now to FIG. 1, ultraviolet light from the lamp 29 is passed alternately through the sample cell 15 and the reference cell 17 as a result of rotation of the chopper 49, which has multiple pairs of openings arranged to effect such alternative light traverse. The unknown gas in which the presence and concentration of oxygen is to be determined is passed into the sample cell by appropriate means, such as by a suitable pump or by the pressure of the patient's exhaled breath in the event of a medical application.

The ultraviolet light passing through the reference gas in the reference cell 17 will result in an output of the photo detector which will remain relatively the same for each pulse. On the other hand, when a pulse of ultraviolet light passes through the sample cell 15, the amount of light detected by the photo diode 55 will depend upon the amount of oxygen present in the cell 15. The signals from the photo detector 55 are applied to the detecting circuit 61 wherein a ratio is determined between the signal during the time the light is passing through the cell 15 and the signal during the time the light is passing through the cell 17. This ratio will be indicative of the oxygen concentration in the sample cell 15. The output of the detecting circuit 61 may then be applied to an indicator 63, either to indicate the ratio or to provide some other number calibrated to the ratio which is indicative of the oxygen concentration. The airtight enclosure 13 is provided so that the interior of the device may be purged of all oxygen other than that which is present in the cell 15.

Referring now to FIG. 2, an alternate embodiment of the invention is illustrated. In FIG. 2, elements having functions essentially identical to those elements in FIG. 1 have been given the same reference number preceded by the numeral 1. The difference between the apparatus illustrated in FIG. 2 and that shown in FIG. 1 is that the gas cell 111 is provided only with a sample chamber 115 and is without a reference chamber comparable to the reference chamber 17 in FIG. 1. In addition, the apparatus of FIG. 8 is devoid of a chopper wheel.

In operating the apparatus of FIG. 2, the HgI arc lamp, instead of being driven at a constant current, is driven by a square wave current source 112. This current source is such that the lower current level has a value approximately 1/5 of that of the higher current level and so that the time averaged current value for the square wave is 2-3 times that of the normally rated current capacity of the lamp. The peak current level is much higher (approximately 1.67 times) than the time averaged value. Under these conditions, as will be further explained in connection with FIG. 3, the bandwidth of the emission curve for the lamp 129 alternates between that shown in FIG. 4 for the lower current and that shown in FIG. 5 for the higher current. During the time the lamp is driven at the lower current, as may be seen in FIG. 4, the emission band does not overlap the 1849.38 angstrom absorption line of oxygen. On the other hand, with the bandwidth as shown in FIG. 5, such overlap does occur.

Without any oxygen present in the chamber 115, the output of the photo detector will be approximately the same for both the high and low current portions of the current from the square wave source 112. However, when oxygen is present in the sample chamber 115, the output of the photo detector during the high current portion of the square wave will be reduced in proportion to the amount of oxygen present in the chamber 115. The detecting circuit 161 in FIG. 2 ratios the outputs of the photo detector for the high current portion of the square wave to the output of the photo detector for the low current portion of the square wave, thereby producing an indication of the concentration of oxygen present in the chamber or cell 115. The ratioing circuit may be similar to that of FIG. 1. Since all other system changes will be common to both the high and low current portions of the square wave and will therefore be cancelled by the ratioing of the outputs by the detecting circuit, no reference chamber is needed. It will be apparent that other modulated wave forms could be used rather than a square wave as described above.

Referring now to FIG. 3, the ultraviolet source 29 is shown in greater detail. The source includes a quartz envelope 165 which includes a central cylindrical section 167, an upper cylindrical section, 169, and a lower cylindrical section 171. The lower cylindrical section has an internal volume substantially smaller than that of the central cylindrical section, such volume being defined by a frusto-conical surface 173 and a roughly spherical surface 175. A narrow neck 177 separates the surface 173 from the surface 175. The outer surface 179 of the lower cylindrical section is provided with a metalized coating 180 and is in contact with an external heat sink 41 appropriately shaped to contain and support the lower cylindrical section 171 of the lamp. A flange 181 extends from one end of the heat sink 41 and is bolted to a suitable support 183 by bolts 185. The current drive 12 is connected to a pair of leads 31 and 33 which, in turn, are connected to internal conductors 187 and 189, respectively, which extend substantially parallel with each other inside of the quartz envelope 185. It is preferred that the central cylindrical section 167 of the envelope 165 be comprised of a quartz which transmits substantially all wavelengths of mercury, such as Suprasil (trademark) quartz. The remainder of the glass envelope may be of any suitable fused quartz.

Each of the conductors 187 and 189 terminates in an arcing electrode 191 and 193, respectively. The arcing electrodes are suitably formed as in any known mercury vapor lamp so as to provide a short arc between the unconnected tips of the electrodes 191 and 193 in a hot zone roughly defined by the dotted line 195. To confine the arc to the hot zone, an insulating spacer 197, typically of quartz, extends the length of the conductors 187 and 189 and substantially all of the length of the electrodes 191 and 193.

It will be noted from FIG. 3 that the lamp shown is positioned, when in the operative condition, in an "upside down" orientation with respect to the usual orientation of mercury arc lamps. Because of the positioning of the heat sink 41 and the lower end of the envelope, with its narrowed shape, a cold zone 199 is created indicated by the dotted line. The cold zone 199 is located near the hot zone 195, but is spaced below it. For reasons which will be explained below, the cold zone 199 serves to condense neutral molecules of mercury, causing them to return to the solid (although acting as a liquid) state within the spherical surface 175, which serves as a mercury reservoir.

The significance of the construction of FIG. 3 lies in the ability to rapidly remove the normally occurring neutral mercury vapor buildup around the electrodes in the hot zone of the arc—typical in known mercury vapor lamps. This normal buildup, when the lamp is operated at a very high current (2-3 times the rated current capacity) can result in the quenching of the 1849.57 angstrom output as described previously.

More particularly, the arc established across the electrodes in the lamp strips away an electron from certain mercury atoms in the vicinity of the arc. These atoms, when regaining the lost electrons, emit photons in the HgI emission spectrum. The number of stripped atoms reaches a saturation level as the vapor pressure of mercury increases in the region of the arc. Once this saturation level is exceeded, the greater proportion of unstripped or neutral atoms in the arc region produce a consequent increase in the absorption of the ultraviolet light emitted from the stripped atoms. In the lamp of FIG. 3, however, such quenching does not occur even when the lamp is run at the higher current levels. This is because the cold zone 199 creates a sharp temperature gradient which results in rapid condensation of mercury vapor except for that in the immediate vicinity of the arc. This condensation has the effect of reducing the proportion of natural atoms relative to activated atoms in the hot zone of the lamp. As long as the arc is maintained, the lamp temperature in the hot zone 195 remains sufficiently high to maintain the vapor state of the activated mercury vapor molecules. The consequence is a substantial broadening of the 1849.57 angstrom emission spectrum of the HgI lamp with minimal quenching from the neutral atoms in the hot zone as shown in FIG. 5. Since the output of the lamp of the invention may therefore be readily broadened without significant self-quenching, the emission of the lamp can be made to overlap significantly the 1849.38 angstrom absorption line of oxygen (see FIG. 5). Typically, wavelength bands FWHM of about 0.50 angstrom units are suitable, and wavelength bands FWHM of up to about one angstrom are achievable.

Although the invention has been described in connection with a mercury arc lamp, it will be apparent to those skilled in the art that other types of low pressure arc lamps may be similarly constructed to take advantage of the spectral line broadening techniques disclosed herein. Thus, arsenic in the singly ionized state emits light at a wavelength of 1890.50 angstroms. Oxygen absorption lines in the Schumann-Runge system are present at 1889.33 angstroms and 1891.33 angstroms (6-0 band of the Schumann-Runge system). An arsenic arc lamp may be broadened in a similar fashion as herein described in order to overlap one or both of such lines and may be employed in the apparatus of either FIGS. 1 or 2 as above-described in connection with mercury.

It may be seen, therefore, that the improved method and apparatus of the invention readily permit the detection and measurement of oxygen concentration using ultraviolet absorption spectroscopy. The use of ultraviolet absorption spectroscopy is made possible by the ability to substantially broaden the emission spectrum of a low pressure extreme ultraviolet arc lamp so as to include the wavelength of at least one of the absorption lines of oxygen in the Schumann-Runge absorption spectrum.

Various modifications of the invention in addition to those shown and described herein will become apparent to those skilled in the art from the foregoing description and accompanying drawings. Such modifications are intended to fall within the scope of the appended claims.

What is claimed is:

1. A method for detecting the presence and amount of elemental oxygen in a sample cell, comprising, passing through the sample cell extreme ultraviolet light from a low pressure arc lamp emitting a wavelength band FWHM of less than about 0.50 angstrom unit, said band overlapping at least one of the Schumann-Runge absorption lines of oxygen at a substantial intensity, detecting the intensity of the ultraviolet light passing through the sample cell, comparing the detected intensity of the ultraviolet light with the intensity of a predetermined non-absorbed condition of said ultraviolet light, and producting a signal proportional to the difference in detected intensities to thereby represent oxygen concentration.

2. A method according to claim 1 wherein said substantial intensity is at least about 20 milliwatts.

3. A method according to claim 1 wherein said non-absorbing condition is achieved by narrowing the wavelength band such that the band does not overlap any Schumann-Runge absorption lines of oxygen at a substantial intensity.

4. A method according to claim 1 wherein said non-absorbing condition is achieved by directing said ultraviolet light through a reference cell which provides a predetermined reference intensity of the light.

5. A method according to claim 1, wherein said extreme ultraviolet light has a bandwidth FWHM of about 0.38 angstrom unit.

6. Apparatus for detecting the presence and amount of elemental oxygen, comprising, a sample cell for containing a gas to be analyzed, a low pressure arc lamp constituting a source of extreme ultraviolet light for passing through the sample cell extremeultraviolet light at a wavelength band FWHM of less than about one angstrom unit, said band overlapping at least one of the Schumann-Runge absorption lines of oxygen at a substantial intensity, detector means for detecting the intensity of the ultraviolet light passing through said sample cell, means for comparing the detected intensity of the ultraviolet light with the intensity of a predetermined non-absorbed condition of said ultraviolet light, and producing a signal proportional to the difference in detected intensities to thereby represent oxygen concentration.

7. Apparatus according to claim 6 wherein said comparing means include means for narrowing the wavelength band emitted from said source such that the band does not overlap any Schumann-Runge absorption lines of oxygen at a substantial intensity to thereby provide the non-absorbing condition.

8. Apparatus according to claim 6 wherein said comparing means include a reference cell containing a gas having a predetermined absorption characteristic, and means for directing ultraviolet light from said source through said reference cell to provide a reference intensity of the light.

9. Apparatus according to claim 6 wherein said source emits extreme ultraviolet light having a bandwidth FWHM of about 0.38 angstrom units.

* * * * *

UNITED STATES PATENT AND TRADEMARK OFFICE
CERTIFICATE OF CORRECTION

PATENT NO. : 4,591,721

DATED : May 27, 1986

INVENTOR(S) : Jacob Y. Wong

It is certified that error appears in the above-identified patent and that said Letters Patent is hereby corrected as shown below:

Column 8, line 15, "producting" should be --producing--.

Signed and Sealed this

Seventh Day of October, 1986

[SEAL]

Attest:

DONALD J. QUIGG

Attesting Officer     Commissioner of Patents and Trademarks